United States Patent [19]

Trenkler et al.

[11] 4,150,284
[45] Apr. 17, 1979

[54] MEDICAL PATIENT CONDITION MONITORING SYSTEM

[75] Inventors: George Trenkler, East Providence, R.I.; Richard G. Delagi, Sharon; Lyle E. McBride, Jr., Norton, both of Mass.

[73] Assignee: Texas Instruments Incorporated, Dallas, Tex.

[21] Appl. No.: 791,899

[22] Filed: Apr. 28, 1977

[51] Int. Cl.$^2$ .............................................. H04B 9/00
[52] U.S. Cl. .................................................... 250/199
[58] Field of Search ......................................... 250/199

[56] References Cited

U.S. PATENT DOCUMENTS

| | | | |
|---|---|---|---|
| 3,898,373 | 8/1975 | Walsh | 250/199 |
| 3,899,429 | 8/1975 | Ueno et al. | 250/199 |

Primary Examiner—Richard Murray
Attorney, Agent, or Firm—Rene' E. Grossman; Andrew M. Hassell; Stephen S. Sadacca

[57] ABSTRACT

A medical patient condition monitoring system includes a portable battery-operable transmitter module which transmits monitored conditions of the patient via infrared energy to the receiver input stage of a medical monitoring and display unit. In one embodiment, the transmitter module which may be worn on the patient's person includes medical electrodes which are coupled to the patient's skin to receive electrical signals generated by the patient's anatomy. A voltage-controlled pulse position modulator circuit is coupled to the medical electrodes for generating pulses controllably positioned in time from a reference frequency in dependence upon the amplitude of the signal generated by the medical electrodes. An infrared light-emitting device is coupled to the output of the pulse position modulator circuit for generating infrared energy bursts in synchronism with the pulses generated by the modulator circuit. A receiver module having an infrared photodetector device located in the patient's room receives the infrared energy, and provides an electrical signal pulsed in synchronism with the bursts of infrared energy. A demodulator circuit coupled to the photodetector device generates an output signal which corresponds to the electrical signals received via the medical electrodes. This output signal is coupled to the monitoring and/or display unit for monitoring the patient's condition.

17 Claims, 13 Drawing Figures

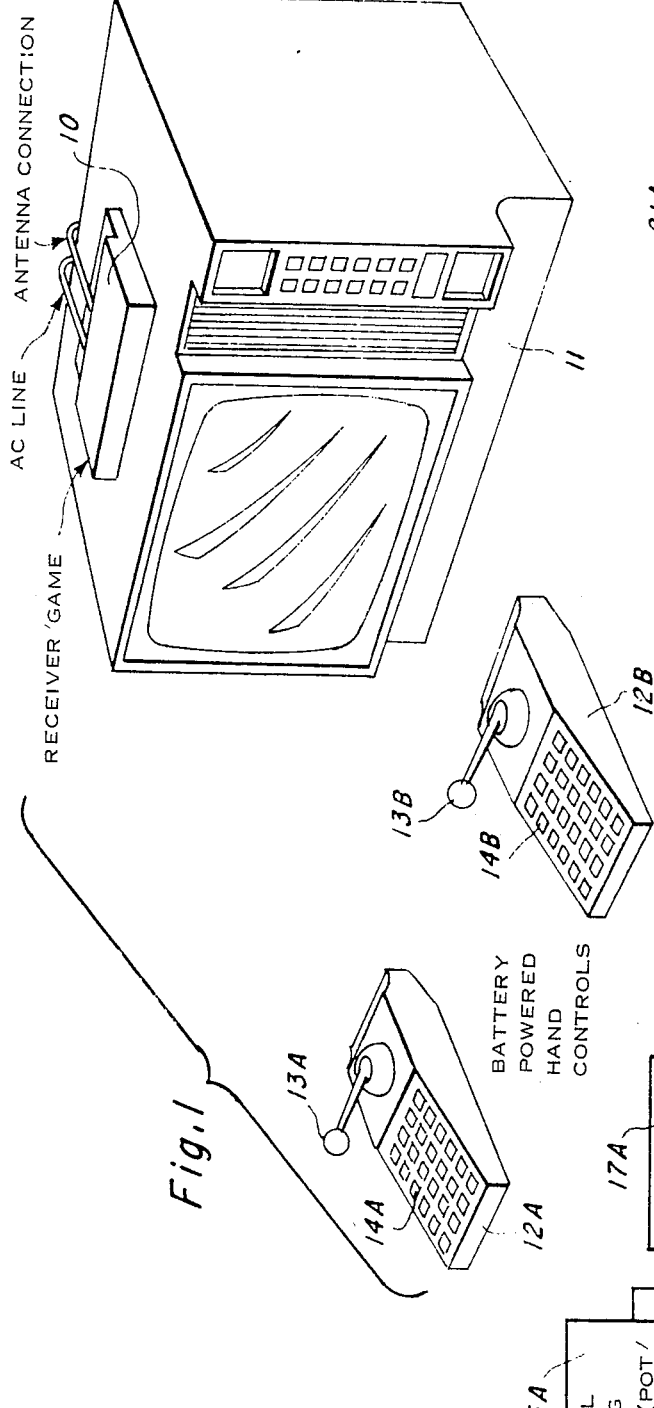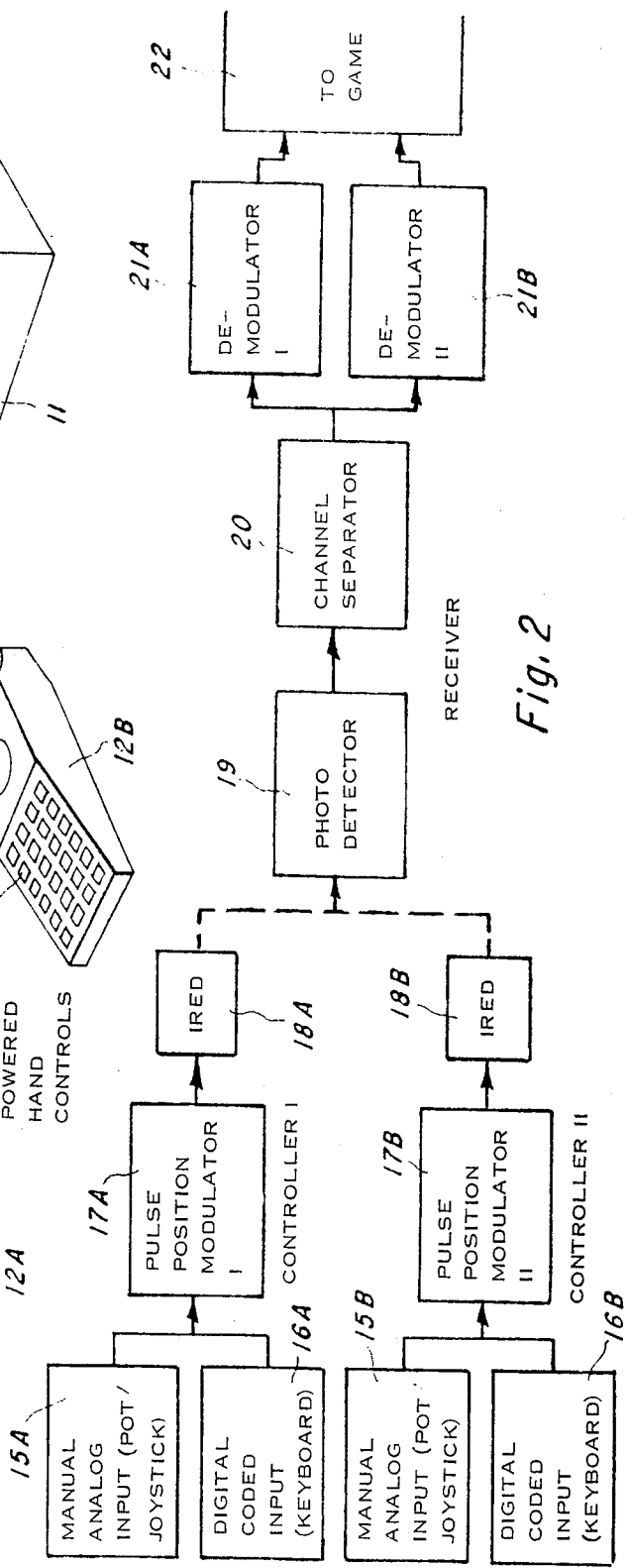

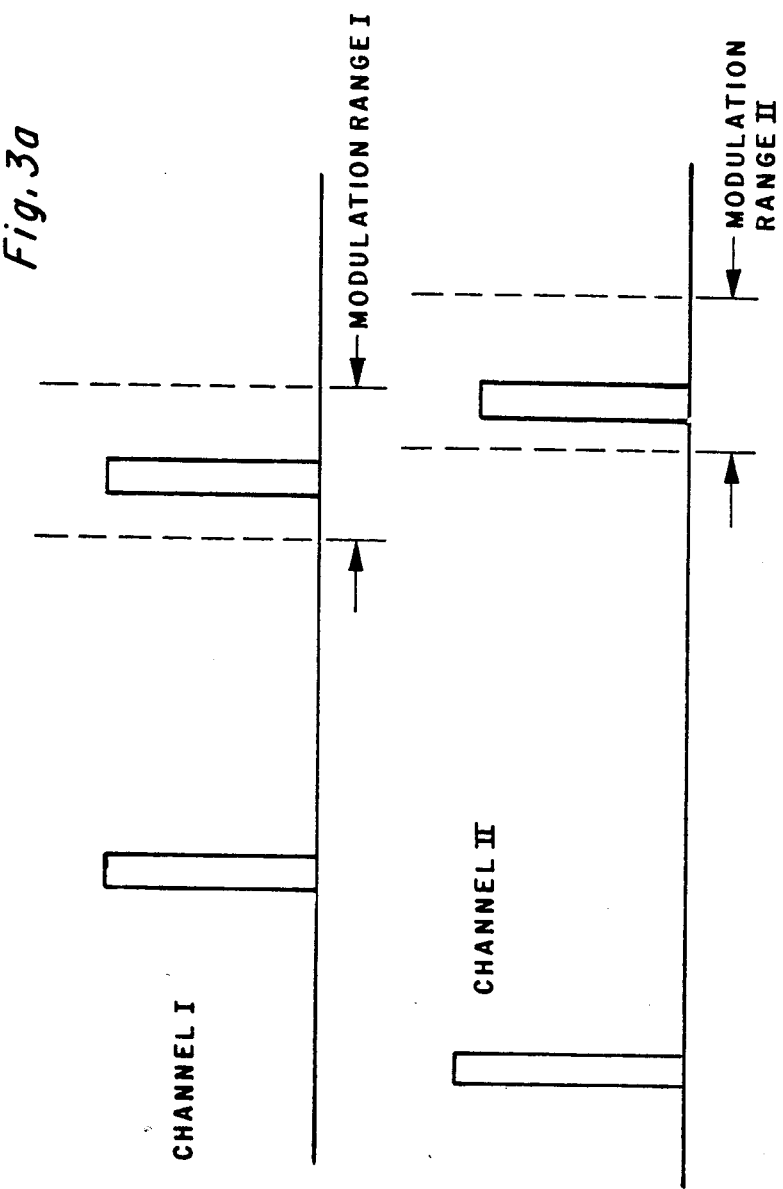

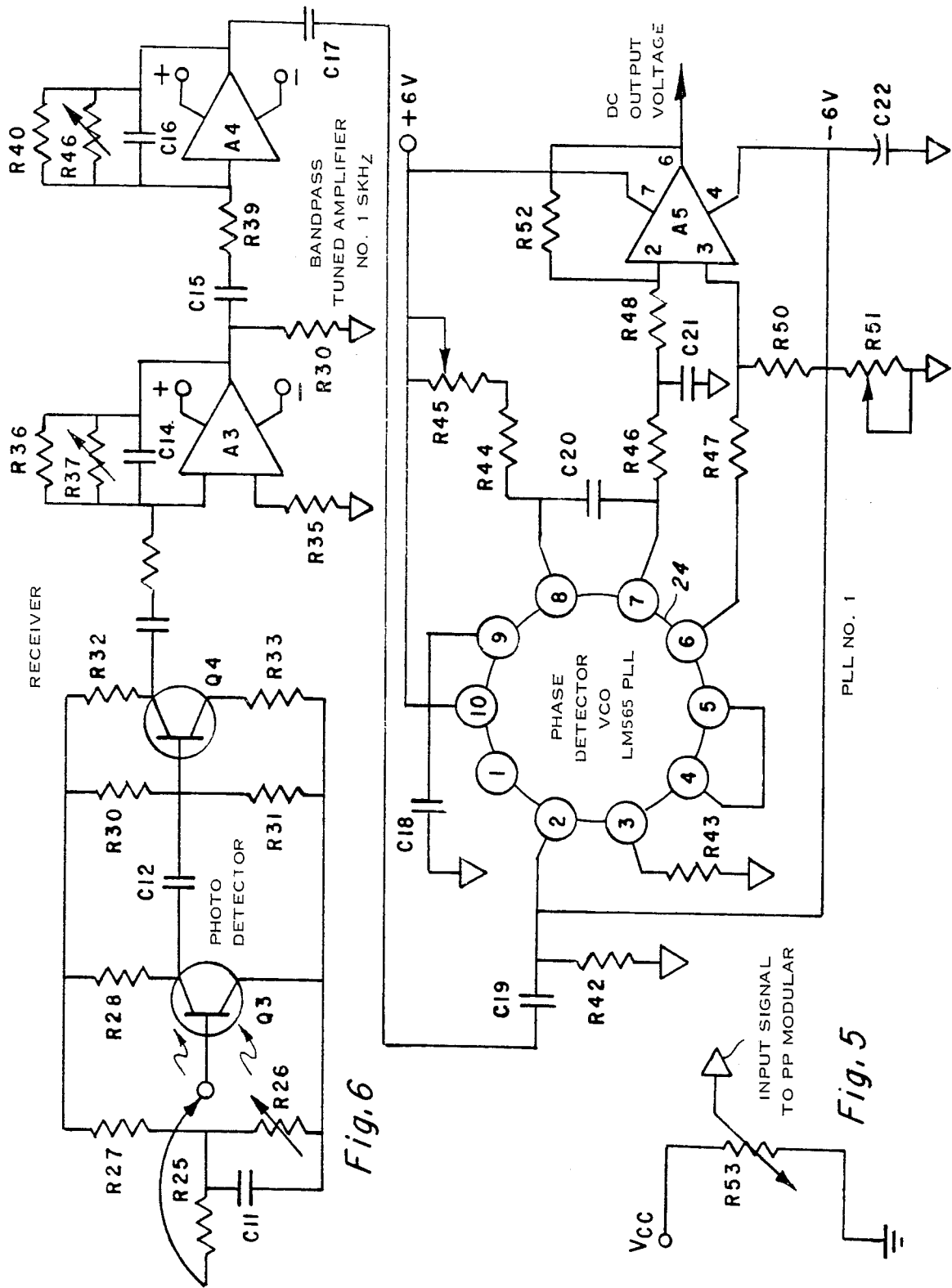

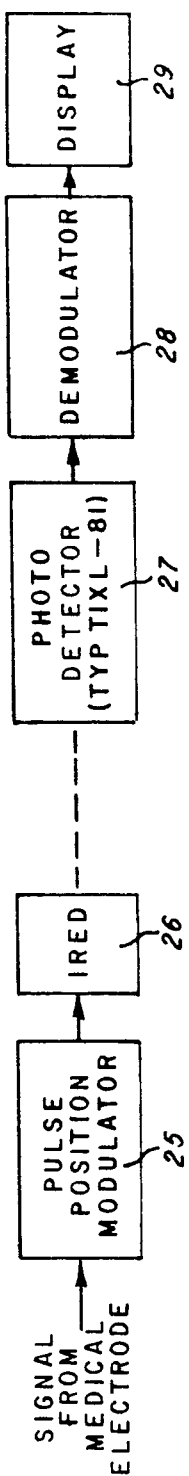
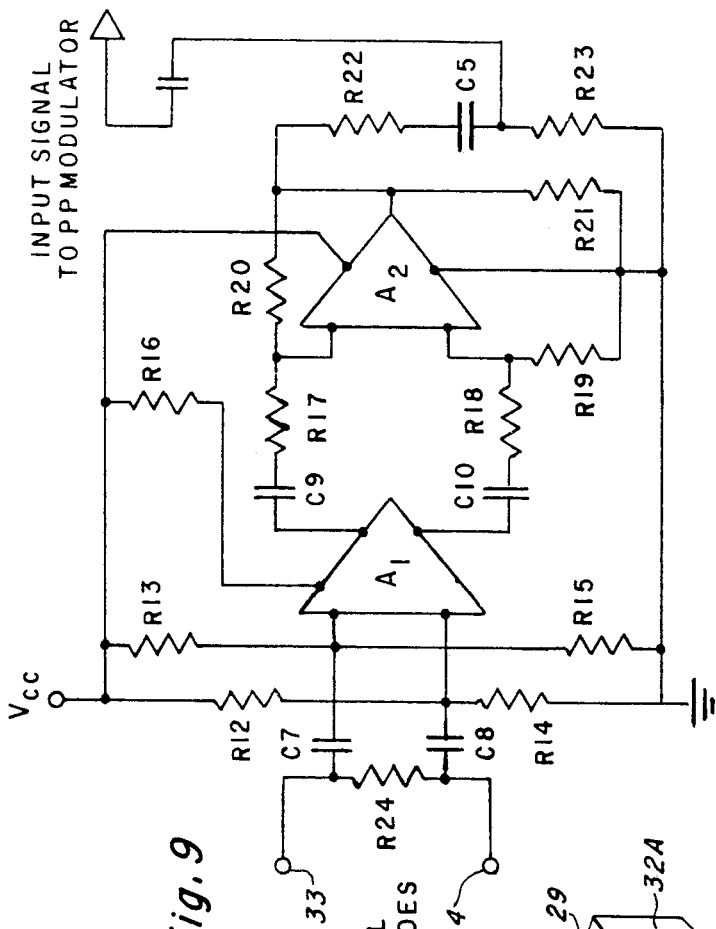
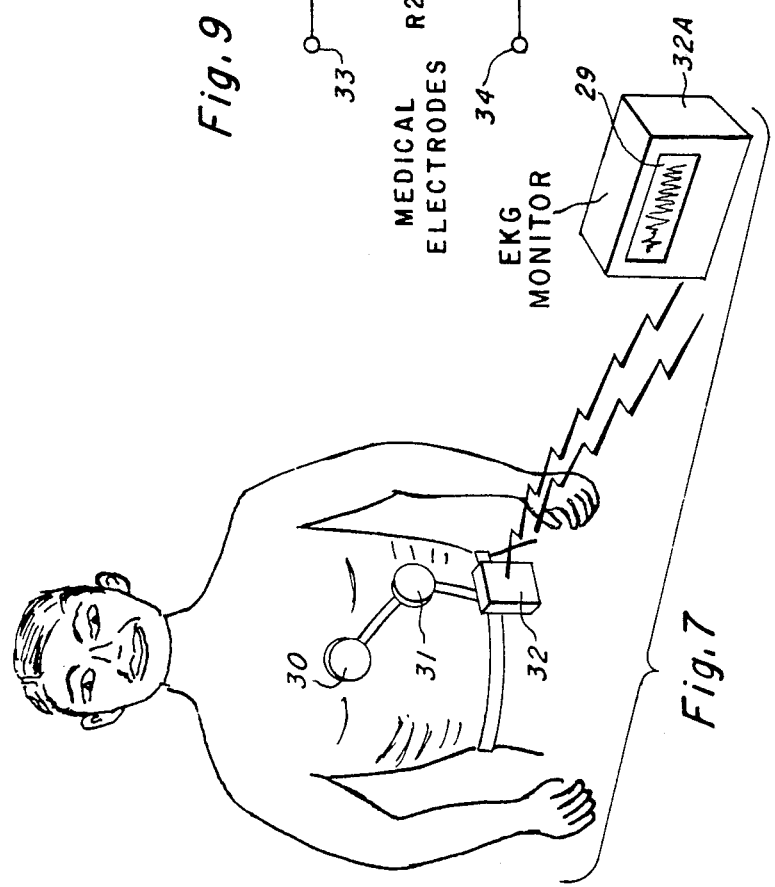

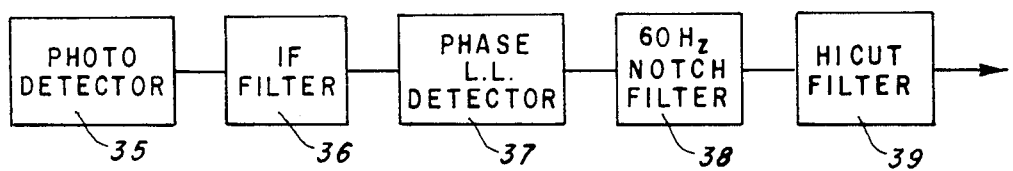
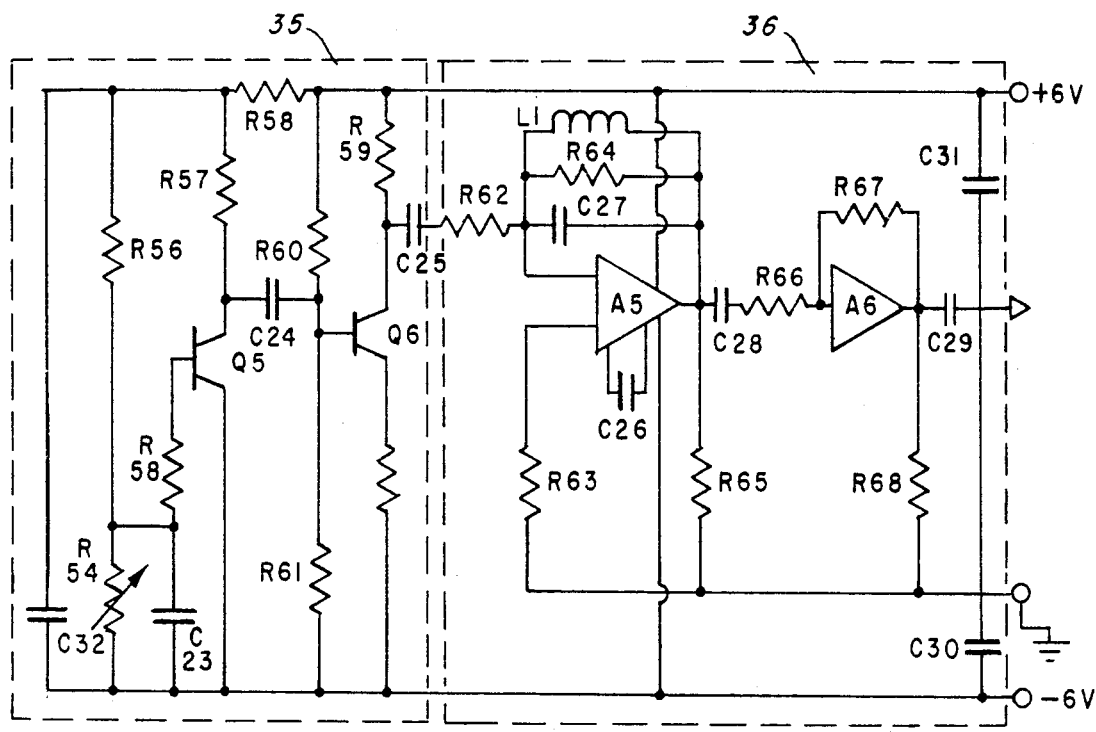

MEDICAL PATIENT CONDITION MONITORING SYSTEM

BACKGROUND OF THE INVENTION

This invention relates to information transmission systems and more particularly to an infrared information transmission system with a portable battery operable transmitter.

Infrared information transmission systems have proved invaluable for short-range transmission of both analog and digital information. The inherent advantages of infrared transmission are apparent; transmission of infrared data does not generate radio frequency interference which might interfere with other instrumentation; and, even more important, the infrared receiver is unaffected by radio frequency interference produced by other devices present. One known system which utilizes infrared transmission of analog information is a music system in which an infrared transmission is connected to a high-fi, stereo or other music production amplifier apparatus, and a portable receiver is incorporated in a headphone set. Music is transmitted via infrared energy anywhere within the confines of the room in which the transmitter is placed. The transmitter of these prior art systems, however, is not portable; the modulated FM plus AM envelope approach utilized, requires a relatively large quantity of power to transmit infrared signal, and therefore, as a practical matter, cannot be operated from battery power with any expectation of a reasonable battery lifetime.

In particular, such applications as a portable transmitter which transmits infrared information from a plurality of sensors or medical electrodes attached to a patient to provide information to a remote monitor, by means other than conventional wires, is not feasible using the prior art system; nor are portable hand-held analog-digital transmitters utilized for video games or television on/off/channel selection capable of being provided utilizing infrared energy transmission. A portable telephone which both receives and transmits information which is connected to the main telephone lines via radio frequency signal transmission is either very expensive or is not capable of eliminating unwanted interference; infrared transmission has not previously been appropriate for this application. In each of the above examples, the transmitter is required to be powered by a small number of batteries making the transmitter not only portable but also containable within a small (hand-held) package.

It is therefore an object of the present invention to provide an improved information transmission system.

Another object of the invention is to provide an improved infrared information transmission system.

A further object of the invention is to provide an infrared information transmission system with a portable transmitter.

Still another object of the invention is to provide an infrared information transmission system with a portable hand-held transmitter powerable by a battery power source.

It is a further object of the invention to provide an improved medical patient monitoring system.

Yet another object of the invention is to provide an improved wireless portable microphone or telephone.

It is yet a further object of the invention to provide an improved hand-held wireless remote control unit for video games, TV set control and the like.

BRIEF DESCRIPTION OF THE INVENTION

These and other objects are accomplished in accordance with the present invention in which an infrared information transmission system utilizes a pulse position modulation technique to transmit analog and/or digital information utilizing sufficiently low power to be operable from a relatively small battery power source.

In one embodiment thereof, the transmitter is comprised of an input device coupled to the input of a voltage controlled pulse position modulation circuit. The pulse position modulation circuit is coupled at its output to an infrared light-emitting device. A switch preamplifier circuit is utilized in some embodiments between the input device and modulation circuit to filter and amplify the input signal from the input device; in some instances, such as the medical application herein described, for example, it is of particular importance that the preamplifier circuit has very high common mode rejection to filter out 60-cycle interference. The pulse position modulator circuit is comprised of a timer coupled to the signal provided by the input device to generate output pulses which deviate from a predetermined frequency by an amount corresponding to the voltage level of the input signal. The input signal may be a variable DC signal or an AC signal. The output of the modulator circuit is coupled to the infrared light-emitting device to activate the device in accordance with the generated output pulses and generate bursts of infrared energy which are in synchronism with the output pulses. The receiver is comprised of an infrared photodetector which receives the bursts of infrared energy and a demodulator circuit which converts the frequency deviation to an output signal. In a preferred embodiment, the demodulator circuit is comprised of a phase locked loop phase detector; the photodetector being coupled to the phase detector by means of an amplifier stage and one or more intermediate frequency filter stages. At the output of the phase locked loop phase detector, a voltage is generated which varies in accordance with the input signal which is generated by the input device. Additional filters may be provided at the output of the phase detector depending on the particular application and environmental conditions.

BRIEF DESCRIPTION OF THE DRAWINGS

Still further objects and advantages of the invention will be apparent from the detailed description and claims when read in conjunction with the accompanying drawings wherein:

FIG. 1 is a perspective view of a video game which incorporates as an integral part thereof the infrared information transmission system of the present invention;

FIG. 2 is a block diagram of the video game of FIG. 1;

FIG. 3a is a graphic representation of the pulses generated over each of two distinct channels for the multiple controllers utilized in the video game of FIG. 1;

FIG. 5 is a detailed circuit diagram of a manual analog input pot utilized in the present embodiment to control the video game of FIG. 1;

FIG. 6 is a circuit diagram of an infrared receiver for the first channel of the video game of FIG. 1, a second similar receiver being provided for the second channel;

FIG. 7 is a perspective view of an EKG monitoring system which incorporates, as an integral part thereof, the infrared information transmission system of the present invention;

FIG. 8 is a block diagram of the EKG monitoring system of FIG. 7;

FIG. 9 is a circuit diagram of a preamplifier/filter circuit utilized to couple a pair of medical electrodes to the pulse position modulator of FIG. 4 in the EKG monitoring system of FIG. 7, the pulse position modulator circuit being substantially the same as that illustrated in FIG. 4;

FIG. 10 is a block diagram of the receiver section of the EKG monitoring system; and FIG. 11 is a circuit diagram of the input section of the receiver utilized in the EKG monitoring system, the phase detector section being similar to that illustrated in FIG. 6.

DETAILED DESCRIPTION OF PREFERRED EMBODIMENTS OF THE INVENTION

Figure 3B:
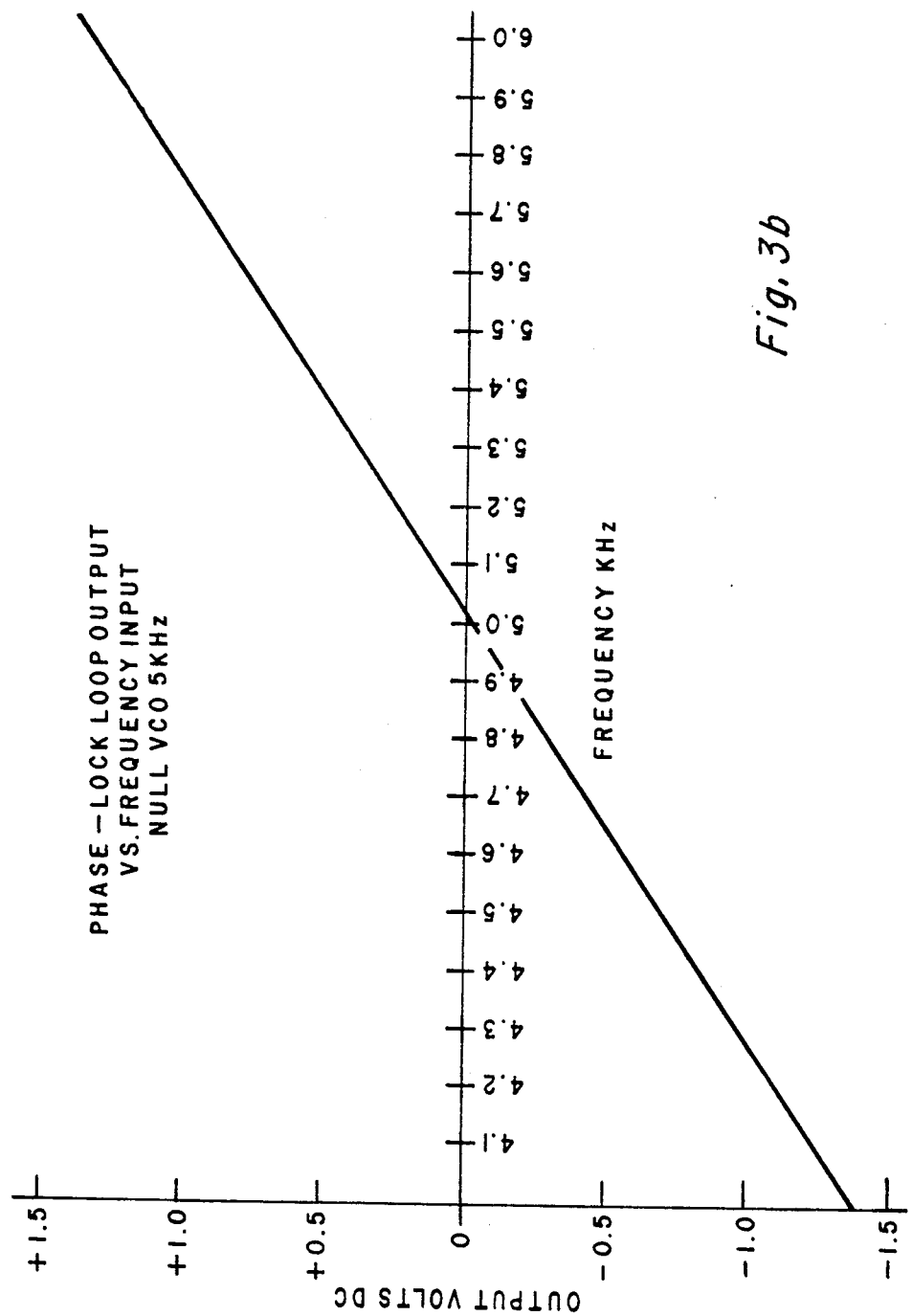
FIG. 3b is a graphic representation of the output signal of the demodulator associated with the first channel.

Referring then to the drawings, two embodiments of the infrared transmission system of the present invention are shown in detail; a video game system embodying the present invention is illustrated in FIG. 1 and a medical condition monitoring system, in particular, an EKG monitoring system embodying the present invention, is illustrated in FIG. 7. The video game system will first be described with respect to FIGS. 1-6.

Referring then to FIG. 1, a video game system is comprised of a main game module 10 housing the video game with an infrared receiver section for receiving and transferring an input control signal to the video game circuit. The output of the video game circuit is coupled to the antenna connection of standard television receiver 11, a pair of battery-powered hand control units 12A and 12B is provided for generating the control signals which are transmitted in the form of infrared energy bursts to the receiver section of main game module 10. Each of the battery-powered hand controls 12A, 12B includes a manual joystick 13A, 13B which may be of the analog (resistor pot controlled voltage) or digital type and may include a keyboard 14A, 14B for entry of additional information generally in digital form. Thus, in accordance with the present invention, the battery-powered hand controls are coupled to the main game module 10 of the video game solely by means of an infrared link rather than the standard cables presently employed in video game systems. In addition, and unlike other systems employing infrared information transmission, hand controls 12A, 12B are portable, operable solely on battery power which, in the described embodiment, may be a single 9-volt transistor radio type battery.

A block diagram of the video game system of FIG. 1 is illustrated in FIG. 2. Referring then to FIG. 2, each of the controllers 12A and 12B include at least one input means which, in the present embodiment, includes a manual analog pot/joystick controlled input circuit 15A, 15B (although, in other embodiments, digital-type joysticks may be utilized) and optionally, digital-coded input devices such as keyboard 16A, 16B. A pulse position modulator circuit 17A, 17B is provided in each of controllers 12A and 12B with an input thereof being coupled to the input means 15A, 15B to receive a variable voltage input signal generated by the input device. Pulse position modulator circuit 17A, 17B includes a timing means for generating pulses controllably positioned in time within a predetermined modulation range from a reference frequency in dependence upon the voltage level of the input signal. The reference frequencies for the controllers 12A and 12B are sufficiently different to prevent overlapping; in the present embodiment, controller 12A is set to a reference frequency of 5 kHz (channel I) and controller 12B is set at a reference frequency of 7 kHz (channel II) as illustrated in the graphic representation of FIG. 3a. An infrared light-emitting device such as a light-emitting diode is coupled to pulse position modulation circuit 17A, 17B for receiving the pulsed output signal, the light-emitting device 18A, 18B generating infrared energy bursts in synchronism with the modulated output pulses.

The receiver is comprised of at least one infrared photodetector 19 which detects the bursts of infrared energy generated by photoemitters 18A and 18B and a channel separator 20 which distinguishes between the signals transmitted from controller 12A and controller 12B. In the present embodiment, as will later be discussed in detail with respect to FIG. 6, separate photodetectors may be provided for each channel, a photodetector for channel I being coupled to a 5-kHz bandpass filter and a second photodetector for channel II being coupled to a 7-kHz bandpass filter. A pair of demodulator circuits 21A and 21B are provided. Demodulator circuit 21A generates an electrical signal indicative of the deviation of the pulses of the modulator output signal from the channel I 5-kHz reference frequency, and demodulator circuit 21B generates an electrical signal indicative of the deviation of the pulses of the modulator output signal from the channel II 7-kHz reference frequency. Thus, demodulator circuit 21A applies a signal indicative of the output of manual analog input joystick 15A to game circuitry 22, and demodulator circuit 21B provides an output signal indicative of the position of manual analog input joystick 15B to video game circuitry 22. The channel I output signal from demodulator circuit 21A, as a function of input frequency deviation, is graphically illustrated in FIG. 3b, and the channel II output signal from demodulator circuit 21B, as a function of input frequency deviation, is graphically illustrated in FIG. 3c.

Figure 4:
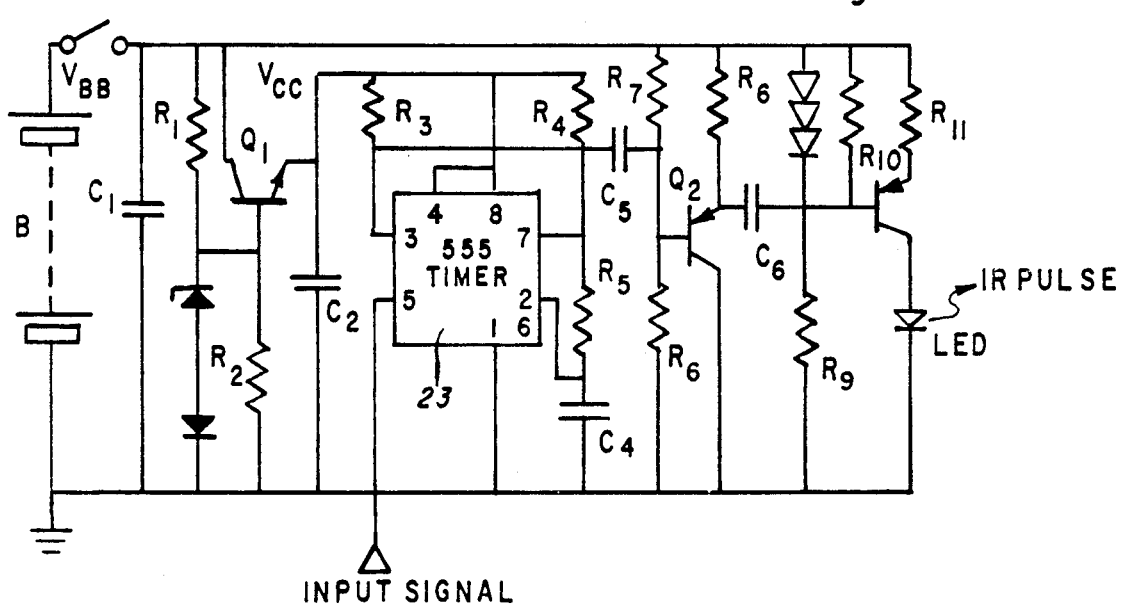
FIG. 4 is a detailed circuit diagram of a universal battery operable infrared transmitter embodied in the present invention.

With reference to FIGS. 4-6, detailed circuit diagrams of the infrared information transmission system, utilized in the video game embodying the present invention, is shown. The transmitter is designated as a universal transmitter as it is capable of providing a pulse position modulated signal from an input signal which is either a variable DC voltage, as utilized in the presently described video game embodiment, or amplitude or frequency modulated AC as will be seen with respect to a medical monitoring system later described herein with respect to FIGS. 7-11.

Referring then to FIG. 4, the transmitter is comprised of a voltage controlled timing circuit 23 such as the SN72555 manufactured and sold as a standard product by Texas Instruments Incorporated, or the LM555 timing circuit manufactured and sold by National Semiconductor. The transmitter is powered by a battery power source B such as a single 9-volt transistor battery (nominal operating voltage of the transmitter being 6-9 V DC). The reference frequency of timer 23 is adjusted by means of resistors $R_4$ and $R_5$ and capacitor $C_4$; thus, for controller 12A, timer 23 is adjusted to 5 kHz, and for controller 12B, timer 23 is adjusted to 7 kHz. Variance in frequency with ambient (temperature) conditions and change of supply voltage is prevented by means of a voltage regulator circuit comprised of diode D1, zener diode D2, resistors R1 and R2, capacitor C2 and transistor Q1 which provides a stable operating voltage $V_{CC}$ from battery voltage $V_{BB}$ provided by battery power source B. The output of timer 23 is a train of pulses selectively modulated from the reference frequency in accordance with the voltage level of input signal provided at terminal 5 of timer 23. The output of timer 23 is provided to the base of transistor Q2 by means of capacitor $C_5$. Transistor Q2 switches transistor Q7 in synchronism with the output of timer 23. Transistor Q7 is switched, capacitor $C_1$ is discharged through transistor Q7, thereby driving infrared light-emitting diode LED with the charge stored in capacitor $C_1$. Light-emitting diode LED thereby generates infrared energy bursts in synchronism with the modulated output pulses from timer 23.

Separate transmitter devices, as shown in FIG. 4, are provided for each of control units 12A and 12B as indicated above. In the present embodiment, a joystick pot 13A, 13B, a circuit diagram of which is illustrated in FIG. 5, is utilized to provide the controlled variable voltage input signal to timer 23. The analog joystick circuit is comprised of a variable resistor R53 coupled between positive supply voltage of low internal impedance and ground to provide a DC signal at its output which varies approximately linearly between the positive supply voltage and ground voltage in dependence upon the position of the joystick 13A, 13B. The joystick, which is now coupled to a video game by means of infrared energy transmission, can, for example, control vertical movement of an image upon the video screen to simulate a racket with which a moving image of a ball is volleyed. By adding additional channels, horizontal as well as vertical positioning is realized; in such instance, additional reference frequencies are utilized; 5 kHz and 7 kHz might be utilized for vertical positioning of the two respective rackets, and 9 kHz and 11 kHz utilized for horizontal positioning of the two respective rackets. Other channels may be utilized for transmitting digital signals from a keyboard, for example. This is accomplished by selective deviation of the transmitted pulses from a preselected reference frequency; for example, a negative deviation might indicate a zero bit and a positive deviation, a one bit. The signals are demodulated in the receiver to determine the activated keys and the game controlled accordingly.

In the presently described two-channel embodiment, two receivers are utilized. Each receiver generates a DC output voltage which is coupled to a control input of the video game electronics 22; these control inputs are the same terminals to which the pot/joystick circuit illustrated in FIG. 5, is normally directed connected to conventional video games by means of a cable.

Figure 3C:
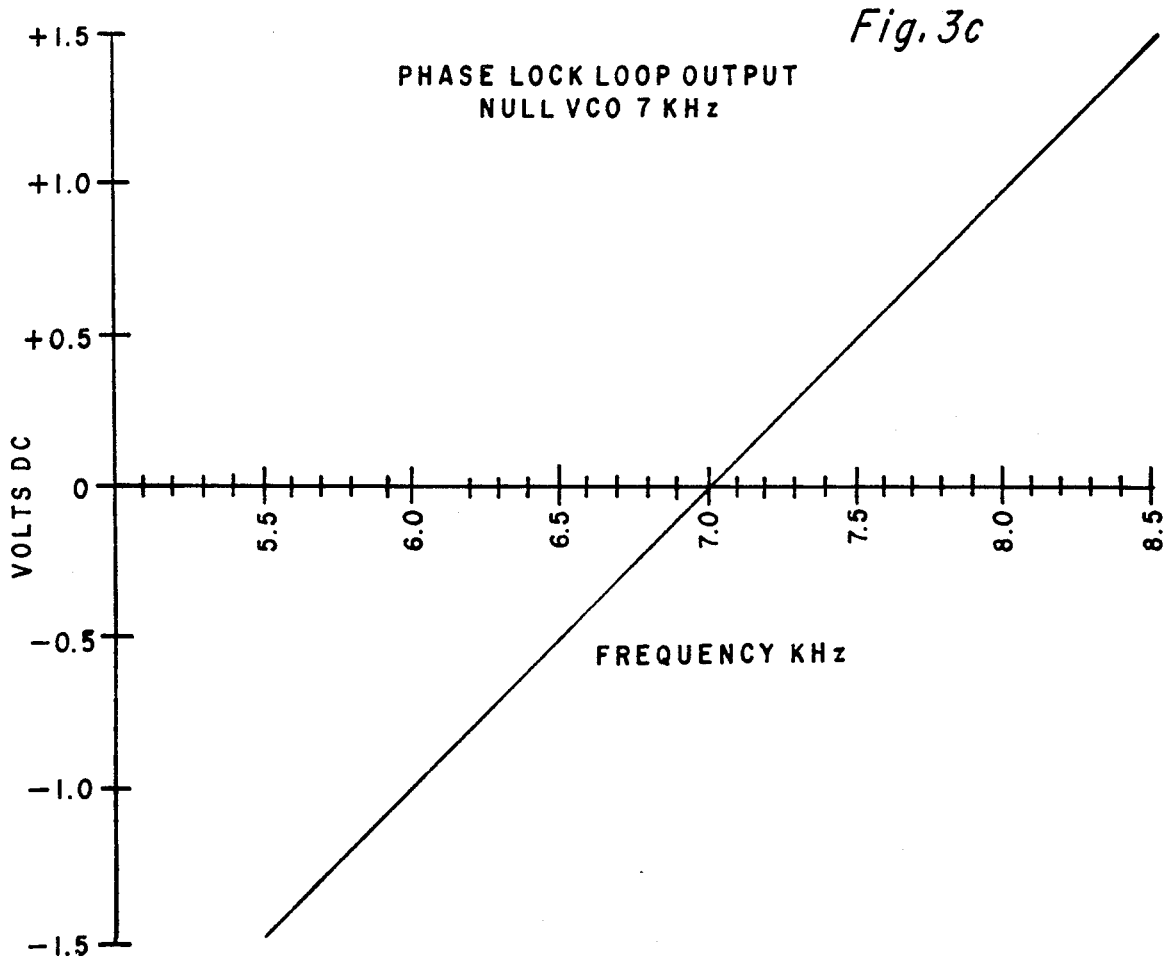
FIG. 3c is a graphic representation of the output signal of the demodulator associated with the second channel.

Referring then to FIG. 6, the receiver includes a photodetector circuit comprises of resistors R25-R28, capacitor C11 and infrared photodetector transistor Q3 which receives the bursts of infrared energy generated by the infrared light-emitting diode LED and provides a pulsed electrical signal via capacitor C12 to a preamplifier circuit. The preamplifier circuit is comprised of resistors R30-R33 and transistor Q4. The output of the preamplifier circuit is transferred via capacitor C13 and resistor R34 to a bandpass tuned amplifier filter comprised of resistors R35-R39, capacitors C14-C17, coils L2 and L3 and operational amplifiers A3 and A4. Bandpass tuned amplifier circuit is tuned to, for example, 5kHz for channel I and 7 kHz for channel II. The filtered signal is then transferred via capacitor C19 to a phase lock loop phase detector 24 which detects the leading edge of the transferred signal. The phase lock loop phase detector may be the LM 565 manufactured and sold as a standard part by National Semiconductor. The adjusted output voltage provided at terminal 7 of detector 24 and a reference voltage provided at terminal 6 of detector 24 are provided to operational amplifier A5 which, in turn, provides the DC output voltage to the video game as discussed above. The voltage controlled output signal from phase locked loop phase detector 24, as previously mentioned, is illustrated in FIG. 3B and 3C for channels I and II, respectively.

Another embodiment of the invention is utilized as an integral part of a medical condition monitoring system, in particular, an EKG monitoring system in which an AC signal derived from the skin of a heart patient in a hospital, etc, is transmitted via infrared energy to a receiver which is located at the patient's room. The receiver may be part of, or remotely located from, heart monitoring equipment by which the patient's condition is determined and monitored. The EKG monitoring system will next be described in detail with respect to FIGS. 7-11.

Referring then to FIG. 7, an EKG monitoring system includes a pair of medical electrodes 30 and 31 which are silver chloride/silver galvanic sensors which sense voltage produced by the body which are on the order of 1 mV. In accordance with the present invention, the medical electrodes are connected to a portable battery-powered infrared transmitter 32 which amplifies and transmits the electrical signals detected by electrodes 30 and 31 to EKG monitor 32A. As shown in the block diagram of FIG. 8, transmitter 32 is comprised of pulse position modulator circuit 25 coupled at its input to the medical electrodes and at its output to infrared light-emitting device 26. EKG monitor 32A includes an infrared photodetector which receives the information transmitted by infrared light-emitting device 26. Photodetector 27 converts the infrared energy into an electrical signal which is demodulated by demodulator circuit 28. The output signal of demodulator 28, which is a representation of the signal provided to the system by medical electrodes 30 and 31, is displayed on a hard or soft copy display 29. Display 29 may be remote from photodetector 27; for example, photodetector 27 may be located in a patient's hospital room while the display may be located at a central monitoring location.

Referring to FIG. 9, a detailed circuit diagram of the input stage of transmitter 32 is shown. Medical electrodes 30 and 31 are connected between terminals 33 and 34, and are coupled to the inputs of differential amplifier A1 by means of capacitors C7 and C8. Amplifier A1 is connected by means of capacitors C9 and C10 and resistors R17 and R18 to a second operational amplifier A2. Amplifiers A1 and A2 serve to amplify the millivolt signal provided by the medical electrodes, and serves as a filter with high common mode rejection, on the order of 100 dB, to substantially filter out 60-Hz interference generated by nearby electrical power lines.

The output signal from amplifier A2 is coupled to the input of the universal pulse position modulator transmitter illustrated in FIG. 4 by means of resistor 22 and capacitor C5. The signal generated by the medical electrodes is on the order of 300 to 400 cycles AC which is the frequency of the input signal to the pulse position modulator circuit of FIG. 4. In this application, timer 23 is adjusted to a reference frequency of 44 kHz. Timer 23 thus generates, at its output, a pulse position modulated signal, the pulses of which are controllably positioned in time from the 44-kHz reference frequency signal by a deviation which depends upon the varying amplitude of the input signal provided by the medical electrodes. The infrared light-emitting device LED is coupled to the output of the output of timer 23 by means of transistors Q2 and Q7, so that the light-emitting device generates infrared energy bursts in synchronism with the pulses output by timer 23.

The receiver is illustrated in the block diagram of FIG. 10. Referring to FIG. 10, infrared photodetector 35 receives the pulse modulator infrared energy bursts generated by the infrared light-emitting diode of the transmitter of FIG. 4 and generates a pulsed electrical signal in synchronism therewith. The output signal from the photodetector is amplified and filtered in an intermediate frequency filter 36, the output signal of which is provided to a phase locked loop phase detector 37. Phase detector 37 generates an electrical signal which, in this embodiment, is an AC signal, the amplitude and frequency of which varies in accordance with the input signal provided by medical electrodes 30 and 31. The output of phase detector 37 is passed through a 60-Hz notch filter 38 which filters out interference which may be caused by lower lines in the vacinity of the receiver and transmitter. Since the frequency of the signal generated by the medical electrodes is in the range of 300 to 400 cycles which is essentially the same frequency signal provided at the output of phase detector 37, a low pass filter 39 is further coupled between the phase locked loop detector and the EKG monitoring equipment.

A detailed diagram of photodetector circuit 35 and intermediate frequency filter 36 is shown in FIG. 11; phase detector 37 is essentially identical to the phase locked loop phase detector circuit illustrated with respect to FIG. 6 and 60-Hz notch filter 38 and low pass filter 39 are of conventional design, and will not here be further described.

The EKG monitoring equipment, which is comprised of a CRT or hardcopy display apparatus, is also of conventional design, and will not be discussed in further detail here.

Referring then to FIG. 11, photodetector circuit 35 is comprised of a phototransistor Q5 which is prebiased by means of resistors R54, R56 and R58. Transistor Q5 provides a pulsed electrical signal in synchronism with the infrared energy bursts transmitted by the infrared LED, via capacitor C24, to the base of amplifying transistor Q6. The amplified output signal from transistor Q6 is transferred by means of capacitor C25 and resistor C62 to intermediate frequency filter 36 which is essentially comprised of a differential amplifier circuit A5 and an operational amplifier circuit A6. The output of operational amplifier circuit A6 is transferred by means of capacitor C29 to a phase locked loop phase detector 37.

The values of the components, as utilized in each of the above-described examples is given below in TABLE I.

Various embodiments of the infrared information transmission system of the present invention as well as systems which include various aspects of such infrared transmission systems as an integral part thereof have now been described in detail. It is contemplated that other systems incorporating the present invention may include a microphone or telephone transmitter as the input device which provides an input signal to the universal transmitter shown and described with respect to FIG. 4 so that such microphone or telephone may be made wireless. The present invention is also adaptable for use in conjunction with any relatively short-distance analog or digital information transmission where it is desirable for the transmitter of such system to be battery operable and portable.

Since it is obvious that many changes and modifications can be made in the above details without departing from the nature and spirit of the invention, it is understood that the invention is not to be limited to said details except as set forth in the appended claims.

TABLE I

| COMPONENT | VALUE | COMPONENT | VALUE | COMPONENT | VALUE |
|---|---|---|---|---|---|
| | | Universal Transmitter | | | |
| R1 | 1.2 KΩ | 7 | 100 KΩ | C2 | 125 μF |
| R2 | 33 Kμ | R8 | 820 ohm | | |
| R3 | 33 KΩ | R9 | 100 KΩ | C4 | ADJ TO f |
| R4 | ADJ TO f | R10 | 16 KΩ | C5 | 2 μF non |
| R5 | 1.8 KΩ | R11 | 2.7 ohm | C6 | 2 μF polar |
| R6 | 33 KΩ | C1 | 640 μF | | |
| | | Medical Electrode Preamplifier/Filter | | | |
| R12 | 220 KΩ | R19 | 220 KΩ | C8 | 1 μF |
| R13 | 220 KΩ | R20 | 220 KΩ | C9 | 1 μF |
| R14 | 51 KΩ | R21 | 47 KΩ | C10 | 1 μF |
| R15 | 51 KΩ | R22 | 680 ohm | C5 | 10 μF |
| R16 | 12 KΩ | R23 | 220 KΩ | A1 | CA-3000 (RCA) |
| R17 | 22 KΩ | R24 | 680 KΩ | A2 | SN² 5741 |
| R18 | 22 KΩ | C7 | 1 μF | | |
| | | Video Game Receiver | | | |
| R25 | 150 KΩ | | | C13 | .1 μF |
| R26 | 15 KΩ | | | C15 | .1 μF |
| R27 | 33 KΩ | R42 | 2.7 KΩ | C17 | .1 μF |
| R28 | 15 KΩ | R43 | 2.7 KΩ | C18 | .008 μF |
| R30 | 330 KΩ | R44 | 5 KΩ | C19 | .1 μF |
| R31 | 27 KΩ | R45 | 10 KΩ | C20 | .001 μF |
| R32 | 5.6 KΩ | R46 | to requirem't | C21 | to requirem't |
| R33 | 270 ohm | R47 | 47 KΩ | C22 | 25 μF |
| R34 | 2.2 KΩ | R48 | 47 KΩ | A2 | SN72748 |
| R35 | 2.2 KΩ | R50 | 390 KΩ | A4 | SN72748 |
| R36 | 39 KΩ | R51 | 100 KΩ | A5 | SN72741 |
| R37 | 330 KΩ | R52 | 470 KΩ | R53 | 5 KΩ |
| R38 | 2.2 KΩ | C11 | 1-2 μF | L1 | 37 mHy |
| R39 | 39 KΩ | C12 | .1 μF | L2 | 37 mHy |
| | | | | L3 | 37 mHy |
| | | Input Stage EKG Receiver | | | |
| R54 | 15 KΩ | R63 | 1 KΩ | C26 | 8 pf |
| R55 | 150 KΩ | R65 | 68 KΩ | C27 | ADJ to f |
| R56 | 100 KΩ | R66 | 1 KΩ | C28 | 1000 pF |
| R57 | 12 KΩ | R67 | 39 KΩ | C29 | .05 μF |
| R58 | 150 KΩ | R68 | 68 KΩ | C30,31 | 10 μF each |
| R59 | 5.6 KΩ | C22 | .1 μF | Q5 | TIL 81 |
| R60 | 330 KΩ | C23 | 1μF | Q6 | 2N930 |
| R61 | 33 KΩ | C24 | 820 pF | A5 | SN72748 |
| R62 | 240 Ω | C25 | .05 μF | A6 | SN72741 |

This invention relates to copending patent applications, Ser. No. 791,913, entitled "Video Game With Portable Control Units" and Ser. No. 791,898, entitled "Low-Power, Infrared Information Transmission System" both by the inventors of the present invention assigned to the assignee of, and filed of even date with, the present application.

What is claimed is:

1. A medical patient condition monitoring system comprising:
   (a) a portable battery-powerable transmitter module including:
      (i) medical electrode means coupleable to the human anatomy for receiving electrical signals generated thereby;
      (ii) battery means for providing power from a battery source to power said transmitter module;
      (iii) a pulse position modulator circuit coupled to said medical electrodes, said pulse position modulator circuit includes timing means for generating pulses controllably positioned in time from a reference frequency in dependence upon the input signal generated by said medical electrode means; and
      (iv) an infrared light-emitting device coupled to said pulse position modulator circuit for receiving pulses generated thereby, said light-emitting device generating infrared energy bursts in synchronism with the pulses generated by said modulator circuit; and
   (b) a receiver module including:
      (i) an infrared photodetector device for altering an electrical signal in accordance with received bursts of infrared energy generated by said light-emitting device to provide an electrical signal pulsed in synchronism with said bursts of infrared energy;
      (ii) a demodulator circuit coupled to said photodetector device for generating an output signal indicative of the deviation of the pulses of said electrical signal from said reference frequency, said output signal corresponding to the electrical signal generated by said medical electrode means; and
      (iii) monitoring means coupled to said modulator circuit, said monitoring means being responsive to said output signal for monitoring and/or displaying the patient's condition.

2. The medical patient condition monitoring system according to claim 1, wherein said medical electrode means is comprised of of a pair of silver chloride/silver galvanic sensors.

3. The medical patient condition monitoring system according to claim 1 including a preamplifier circuit coupling said medical electrode means to said pulse position modulator circuit.

4. The medical patient condition monitoring system according to claim 1 including filter means having high common mode rejection coupling said medical electrode means to said modulator circuit for filtering out AC interference generated by power lines in the vicinity of said transmitter module.

5. The medical patient condition monitoring system according to claim 1 including voltage regulator means for coupling a battery power source to said pulse position modulator circuit, said voltage regulator means providing an approximately stable reference voltage to said timing means regardless of variations in ambient conditions to thereby provide an approximately stable reference frequency for said timing means.

6. The medical patient condition monitoring system according to claim 1 including driver circuit means coupling said pulse position modulator circuit to said infrared light-emitting device.

7. The medical patient condition monitoring system according to claim 1, wherein said driver circuit means includes capacitor means for storing a charge during time periods when no pulse is being transmitted by said modulator circuit and for discharging into light-emitting device upon the occurrence of pulses generated by said modulator circuit.

8. The medical patient condition monitoring system according to claim 1 including amplifier means coupling said photodetector device to said phase detector circuit.

9. The medical patient condition monitoring system according to claim 1 including a bandpass filter, tuned to said reference frequency, coupling said photodetector device to said phase detector circuit.

10. The medical patient condition monitoring system according to claim 1, wherein said phase detector circuit is a phase locked loop phase detector circuit.

11. The medical patient monitoring system according to claim 1 including a notch filter coupling said phase detector circuit to said medical monitoring unit for rejecting AC interference from power lines in the vicinity of the receiver unit, said notch filter being tuned to the frequency of the AC interference.

12. The medical patient condition monitoring system according to claim 1 including a low pass filter coupling said phase detector circuit to said monitoring means for rejecting high frequency noise transferred in the output signal from said phase detector circuit.

13. The medical patient condition monitoring system according to claim 1, wherein said monitoring means includes a video display device for displaying the patient's condition.

14. The medical patient condition monitoring system according to claim 1, wherein said monitoring means includes a hard-copy recording device for recording the patient's condition.

15. The medical patient condition monitoring system according to claim 1, wherein the patient's EKG is monitored by said system.

16. The medical patient condition monitoring system according to claim 1, wherein said transmitter module includes means for fastening said transmitter module to the anatomy of the patient.

17. The medical patient condition monitoring system according to claim 1 including a plurality of transmitter and receiver modules wherein the receiver modules are located in respective patients' rooms, and wherein the each of the monitoring means are located at a central location.

* * * * *